(12) United States Patent
Wujek et al.

(10) Patent No.: US 8,911,758 B2
(45) Date of Patent: Dec. 16, 2014

(54) INSECTICIDE FORMULATIONS

(75) Inventors: Dennis G. Wujek, Zionsville, IN (US); Raymond E. Boucher, Jr., Lebanon, IN (US); Martin C. Logan, Indianapolis, IN (US); Stephen L. Wilson, Zionsville, IN (US); Mei Li, Westfield, IN (US); Lorenzo Aulisa, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/370,425

(22) Filed: Feb. 10, 2012

(65) Prior Publication Data

US 2012/0207807 A1     Aug. 16, 2012

Related U.S. Application Data

(60) Provisional application No. 61/442,003, filed on Feb. 11, 2011.

(51) Int. Cl.
| | |
|---|---|
| *A01P 7/04* | (2006.01) |
| *A01N 25/28* | (2006.01) |
| *A01N 57/16* | (2006.01) |
| *A01N 25/10* | (2006.01) |

(52) U.S. Cl.
CPC .............. *A01N 25/28* (2013.01); *A01N 57/16* (2013.01)
USPC ........................................... 424/409; 514/89

(58) Field of Classification Search
CPC .................................................. A01N 25/28
USPC ......................................... 424/408, 417, 409
See application file for complete search history.

(56) References Cited

U.S. PATENT DOCUMENTS

| | | | |
|---|---|---|---|
| 4,557,755 A | 12/1985 | Takahashi et al. | |
| 4,670,246 A * | 6/1987 | Dahl et al. ................... | 424/419 |
| 4,889,719 A | 12/1989 | Ohtsubo et al. | |
| 5,834,290 A | 11/1998 | Egelrud et al. | |
| 5,866,153 A * | 2/1999 | Hasslin et al. ................ | 424/408 |
| 2008/0176745 A1 * | 7/2008 | Wilson et al. ................. | 504/101 |
| 2010/0226950 A1 * | 9/2010 | Wilson .......................... | 424/408 |
| 2011/0052654 A1 * | 3/2011 | Wilson et al. ................. | 424/408 |
| 2012/0129694 A1 * | 5/2012 | Ditmarsen et al. ........... | 504/107 |

FOREIGN PATENT DOCUMENTS

| | | |
|---|---|---|
| CN | 101731210 | 6/2010 |
| JP | 09249505 * | 9/1997 |
| WO | 9614743 A1 | 5/1996 |
| WO | 0005962 A1 | 2/2000 |
| WO | 2006092409 A2 | 9/2006 |
| WO | WO2007-072052 | 6/2007 |
| WO | WO2009-097860 | 8/2009 |
| WO | WO2010-101820 | 9/2010 |
| WO | WO2010101820 * | 9/2010 |
| WO | 2011017480 A2 | 2/2011 |

OTHER PUBLICATIONS

PCT International Search Report and Written Opinion, International Application No. PCT/US2012/024597, mailed Sep. 27, 2012.

* cited by examiner

*Primary Examiner* — Audrea Buckley
(74) *Attorney, Agent, or Firm* — Carl D. Corvin; TraskBritt, PC.

(57) ABSTRACT

Insecticide formulations having improved chemical and physical stability and related methods are disclosed. The insecticide formulations may include a plurality of microcapsules, each including at least one organophosphate insecticide (e.g., chlorpyrifos-methyl) at least partially surrounded by a polymer shell. The insecticide formulations may be used to control insect populations by singular or periodic applications. The microcapsule polymer shell of the insecticide formulations may be formed by combining a cross-linking amine and a hydrophobic monomer (e.g., an isocyanate) at a molar ratio of amine to isocyanate groups of less than about 1:1.

27 Claims, 1 Drawing Sheet

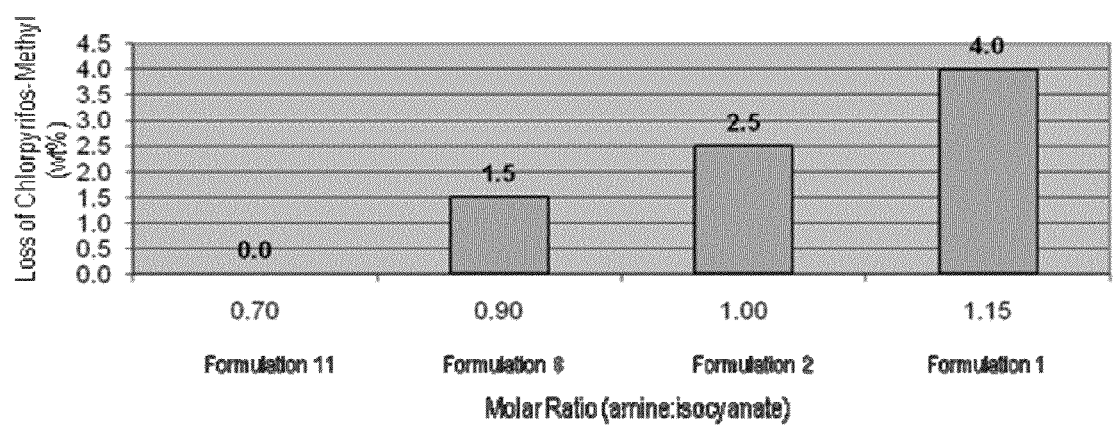

INSECTICIDE FORMULATIONS

CROSS-REFERENCE TO RELATED APPLICATION

This application claims the benefit of U.S. Provisional Patent Application Ser. No. 61/442,003, filed Feb. 11, 2011, the disclosure of which is hereby incorporated herein in its entirety by this reference.

TECHNICAL FIELD

Various aspects and embodiments relate generally to formulations of insecticide formulations that exhibit advantageous biological, commercial and/or environmental properties.

BACKGROUND

Controlling insect population is essential to modern agriculture, food storage, and hygiene. Currently, safe and effective encapsulated insecticidal formulations play a significant role in controlling insect populations. Properties of useful encapsulated insecticidal formulations include good efficacy against targeted pests, including good initial toxicity against targeted insects, ease of handling, stability, advantageous residence times in the environment and, in some instances, a long effective period of insecticidal activity after its application to an area adjacent to a population of insects.

Unfortunately, most insecticides formulations, especially liquid-based preparations, lose their efficacy relatively soon after their application. Such insecticide formulations must, therefore, be reapplied to ensure insect control. Additionally, formulations with a short period of post-application activity may result in periods of time during which a surface adjacent to a population of insects is vulnerable to infestation. This creates a need to periodically apply various insecticidal formulations in order to control continuing pest infestations or to prevent their occurrence, increase the amount of insecticides that must be used, and the increased cost associated with their shipping, handling and application.

BRIEF SUMMARY

Embodiments of the present disclosure include insecticide formulations. Such insecticide formulations may include a polymer shell formed from a mixture comprising a cross-linking amine and a hydrophobic isocyanate monomer, where the molar ratio of amine to isocyanate groups in the mixture is between about 0.3 to 1 and about 0.8 to 1, and an insecticide at least partially encapsulated by the polymer shell.

Embodiments of the present disclosure also include insecticide formulations formed by a process that includes forming an organic (i.e., oil) phase consisting of a hydrophobic monomer, at least one insecticide composition, a solvent, and a preservative, combining the organic phase with an aqueous phase to form a dual-phase mixture and combining at least one cross-linking amine with the mixture to form the insecticide capsule formulation.

Embodiments of the present disclosure further include methods of forming insecticide formulations. The methods may include forming an organic phase consisting of a hydrophobic monomer, at least one insecticide composition, a solvent, and a preservative, combining the organic phase with an aqueous phase to form a mixture and combining at least one cross-linking amine with the mixture to form the insecticide capsule formulation.

Embodiments of the present disclosure further include methods of extending the effective field life of an insecticide. Such methods may include combining the insecticide, a cross-linking amine, and at least one isocyanate monomer, the cross-linking amine and the at least one isocyanate monomer are present in concentrations such that the molar ratio of the cross-linking amine to isocyanate groups contained in the mixture is between about 0.3:1 and about 0.8:1, and forming a polymer shell that at least partially encapsulates a portion of the insecticide.

Embodiments of the present disclosure further include a stable aqueous insecticide formulation that includes a) a microcapsule, having a water insoluble polyurea shell wall prepared by an interfacial polycondensation reaction between a water soluble cross-linking amine and an oil soluble isocyanate monomer in which (i) the molar ratio of amine to isocyanate groups is between about 0.3 to 1 and about 0.8 to 1, (ii) the polyurea shell has a thickness of greater than about 2 nanometers (nm) and less than about 50 nm, (iii) the average particle size is from about 1 micrometer ($\mu m$) to about 30 $\mu m$, and (iv) containing an inner liquid core comprised of an insecticide at least partially encapsulated by the polymer shell; and b) a continuous aqueous phase.

BRIEF DESCRIPTION OF THE DRAWING

FIG. 1 is a bar graph showing degradation of chlorpyrifos-methyl in insecticide formulations formed according to embodiments of the methods of the present disclosure.

DETAILED DESCRIPTION OF THE INVENTION

As used herein, the terms "encapsulate," "encapsulated" and "encapsulation" mean and include to surround, encase, or protect in a capsule.

As used herein, the term "microcapsule" means and includes a particle(s) of the insecticide encapsulated within a polymeric material, such as polyurea.

As used herein, the terms "shell" and "wall" mean and include an assembly of a polymeric material, such as polyurea, disposed on or encapsulating a surface of a core including an insecticide. Such terms do not necessarily imply that a given shell or wall is completely uniform or that it completely encompasses whichever materials or components that are localized within the corresponding microcapsule.

As used herein, the term "chlorpyrifos-methyl" refers to O,O-dimethyl-O-3,5,6-trichloro-2-pyridyl phosphorothioate.

Embodiments of insecticidal formulations include an insecticide at least partially encapsulated within a polyurea shell (i.e., a microcapsule). The insecticide within the shell may be present as a stable aqueous capsule suspension of an organophosphate insecticide (e.g., chlorpyrifos-methyl). The insecticidal formulations provide effective pest control with improved chemical and physical stability. For example, the insecticidal formulations may effectively kill or repel insects for at least 14 days after their application. Such improved stability may be obtained by using a cross-linking amine and an isocyanate monomer to form the microcapsule polyurea shell where the molar ratio of amine:isocyanate groups is less than about 1:1. Methods of forming the insecticidal formulations and methods of controlling (e.g., repelling, inhibiting or killing) pests using the insecticidal formulations are also disclosed.

The insecticide may include at least one organophosphate insecticide, such as, acephate, azinphos-methyl, chlorfenvinphos, chlorethoxyfos, chlorpyrifos, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and/or trichlorfon. As a non-limiting example, the ingredient having the insecticidal activity may be chlorpyrifos-methyl.

Chlorpyrifos-methyl, which is the common name for O,O-dimethyl O-3,5,6-trichloro-2-pyridyl phosphorothioate, is a well known insecticide that has been show to be effective against a broad spectrum of pests. Chlorpyrifos-methyl is a crystalline organophosphate insecticide that acts as an acetylcholinesterase inhibitor, killing insects by interfering with the function of the nervous system. For example, insecticide compositions including chlorpyrifos-methyl are marketed by Dow AgroSciences LLC (Indianapolis, Ind.) under the trade name RELDAN®.

The shell that at least partially encases the insecticide may be formed by a reaction (e.g., an interfacial polycondensation reaction) between at least one monomer that is essentially insoluble in water (i.e., a hydrophobic monomer) and at least one monomer that is soluble in water (i.e., a hydrophilic monomer). Examples of hydrophobic monomers that may be used to form the shell of the microcapsule include, but are not limited to isocyanates, diisocyanates, polyisocyanates, diacid chlorides, poly acid chlorides, sulfonyl chlorides and chloroformates. The term isocyanate as used herein may include isocyanates, diisocyanates, polyisocyanates and mixtures thereof. As a non-limiting example, the hydrophobic monomer may be an isocyanate such as PAPI™ 27 polymethylene polyphenylisocyanate, which is marketed by Dow Chemical Company (Midland, MI).

Examples of hydrophilic monomers that may be used to form the shell of the microcapsule include, but are not limited to, cross-linking amines such as diamines and polyamines, water-soluble diols and water-soluble polyols. The capsule forming reaction may be carried out in the presence of a cross-linking amine. For example, a polyurea shell may be formed by reacting a hydrophobic isocyanate monomer and the cross-linking amine. Examples of cross-linking amines that may be used to form the shell of the microcapsule include, but are not limited to, ethylenediamine (EDA), diethylenetriamine (DETA), tetramethylenediamine, N,N',-dimethyl piperazine, N-ethylpiperazine 1,2-cyclohexyldiamine, triethylenetetramine and piperazine.

During polymerization, the cross-linking amine may hasten shell formation. While not wishing to be bound by any particular theory, it is believed that the cross-linking amine may also degrade the organophosphate insecticide during the shell forming reaction. Thus, it has been discovered that using a cross-linking amine and a hydrophobic isocyanate monomer where the molar ratio of amine:isocyanate groups in the mixture is less than or equal to about 1:1 provides a chemically and physically stable system with decreased degradation of the organophosphate insecticide. The molar ratio of amine:isocyanate groups in the mixture used to prepare the insecticide formulation may be between about 0.1:1 and about 1:1, and more particularly between about 0.3:1 and about 0.8:1. By way of example and not limitation, the molar ratio of amine:isocyanate groups in the mixture used to prepare the insecticide formulation may be about 0.7:1.

The insecticide formulations may be prepared, for example, using an emulsion polymerization process that includes combining an aqueous phase that includes the hydrophilic monomer (e.g., the cross-linking amine) into an organic phase that includes the hydrophobic monomer (e.g., the isocyanate) and the insecticide. The hydrophobic monomer and the hydrophilic monomer are reacted to form a polymeric shell around a core of the insecticide dispersed within a liquid. The insecticide formulations may be prepared by a batch process, an in-line or continuous process or a combination of the two. Such processes may be designed, optimized to the desired output parameters and operated by one of ordinary skill in the art.

For example, the aqueous phase may be prepared by dissolving one or more additives, which may be included in the aqueous phase of the insecticide formulations. Such additives may include one or more surfactants and preservatives. An example of a suitable surfactant includes, but is not limited to, polyvinyl alcohol (PVA), such as GOHSENOL® GL03 polyvinyl alcohol, which is commercially available from Nippon Synthetic Chemical Industry Co. (Osaka, Japan). An example of a suitable preservative includes, but is not limited to, PROXEL® GXL preservative (Arch UK Biocides Limited, England). For example, GOHSENOL® GL03 polyvinyl alcohol and PROXEL® GXL preservative may optionally be added to the aqueous phase.

The organic or oil phase may be formed by combining PAPI™ 27 polymethylene polyphenylisocyanate with a solution of the chlorpyrifos-methyl in a solvent. The solvent may be a hydrocarbon fluid, such as SOLVESSO™ 150 ND, which is a mixture of aromatic hydrocarbons with a distillation temperature range of between about 185° C. and about 207° C. that is commercially available from Exxon Mobile Chemical Company (Houston, TX). For example, the solution of the chlorpyrifos-methyl in the solvent may be formed to include about 50 wt % of the chlorpyrifos-methyl in the SOLVESSO™ 150 ND. A commercially available composition of chlorpyrifos-methyl may also be used in the organic phase. Such compositions, such as RELDAN® insecticide, which is marketed by Dow AgroSciences LLC, may include between about 10 wt % and about 30 wt % of the chlorpyrifos-methyl.

The organic phase may also include a preservative, such as 1-nonanal. The ingredients of the organic phase may be mixed until a substantially homogenous suspension is obtained.

The aqueous phase and the organic phase may be combined to form a mixture that includes two immiscible phases (i.e., a dual-phase mixture). The dual-phase mixture may be subjected to a conventional high shear emulsification process to disperse the oil phase into the aqueous phase. As the oil phase is dispersed in the aqueous phase, a plurality of particles of the oil phase may form within the aqueous phase. The emulsification process may be continued until a desired particle size (i.e., the volume mean diameter of the particles) is achieved. Thus, the particle size may be controlled by adjusting at least one of a length of time or a speed at which the mixture is subjected to emulsification. For example, the particle size may be between about 1 micron ($\mu$m) and about 30 $\mu$m and, more particularly, between about 1 $\mu$m and about 10 $\mu$m.

The cross-linking amine, such as the EDA, may then be added to the emulsion and may react with isocyanate groups of the hydrophobic monomer, such as the PAPI™ 27 polymethylene polyphenylisocyanate, at an interface between the oil phase particles and the aqueous phase to form the microcapsule polyurea shell. As a non-limiting example, the molar ratio of amine to isocyanate groups in the mixture may be between about 0.3:1 and about 0.8:1 and, more particularly, between about 0.5:1 and about 0.7:1. After addition of the cross-linking amine, the mixture may be maintained at a temperature of between about 20° C. and about 60° C. and, more particularly, between about 20° C. and about 30° C.

The resulting insecticidal capsule formulation is a microcapsule suspension that includes the oil phase liquid particles at least partially encapsulated by the shell and suspended in the aqueous phase. The oil phase particles may be referred to herein as the "core" of the microcapsules. In embodiments in which the hydrophobic monomer comprises an isocyanate and the cross-linking amine comprises EDA, the shell of the microcapsules may comprise a polyurea. By adjusting the length of time during which the mixture is subjected to emulsification and/or a speed of mixing, a thickness of the polyurea shell may be varied. Similarly, the amounts of isocyanate, cross-linking amines, and other ingredients may be adjusted to form capsules with varying sizes and shell thicknesses.

The processing method used to prepare the insecticide formulations may be a combination of a batch process and a continuous, in-line emulsification process. The organic and aqueous phases may be prepared as described herein and may then be individually metered into an inline rotor/stator homogenizer, or similar device, at an aqueous to oil volume ratio of about 0.75 to about 1.10. The size of the emulsion oil droplet formed may be controlled by the feed rates into the homogenizer and the rotational speed of the homogenizer. For example, the particle size may be between about 1μm and about 30μm and, more particularly, between about 1μm and about 10μm. The cross-linking amine solution may then be added in-line to the out-flow of the emulsion from the homogenizer using another metering system to add the second component for the polyurea shell formation. The resulting stream may then be collected into a finishing vessel where any finishing agents, as described herein, may be added to complete the formulation. The PAPI™ 27 isocyanate may alternatively be added as a separate stream to the homogenizer by adding another metering system. The processing described herein may be designed, optimized and operated by one of ordinary skill in the art.

The calculation of the amounts of capsule wall components needed to achieve a target wall thickness was based on the geometric formula relating the volume of a sphere to its radius. If a core-shell morphology is assumed, with the core comprised of the non wall-forming, water-insoluble components (i.e., the chlorpyrifos-methyl and the solvent) and the shell made up of the polymerizable materials (i.e., the isocyanate and the amine), then equation (1) holds, relating the ratio of the volume of the core ($V_c$) and the volume of the core, plus the volume of the shell ($V_s$) to their respective radii, where $r_s$ is radius of the capsule including the shell and $l_s$ is thickness of the shell.

$$\frac{V_C + V_S}{V_C} = \left(\frac{r_s}{r_s - l_s}\right)^3 \quad (1)$$

Solving equation (1) for the volume of the shell yields:

$$V_s = V_c\left(\left(\frac{r_s}{r_s - l_s}\right)^3 - 1\right) \quad (2)$$

Substituting masses ($m_i$) and densities ($d_i$) for their respective volumes ($m_s/d_s = V_s$ and $m_c/d_c = V_c$, where the subscript s or c refers to the shell or core, respectively) and solving for the mass of the shell gives:

$$m_s = m_c \frac{d_s}{d_c}\left(\left(\frac{r_s}{r_s - l_s}\right)^3 - 1\right) \quad (3)$$

In order to simplify the calculation and directly use the respective weights of the core and shell components, the approximation that the density ratio $d_s/d_c$ is approximately equal to one was made yielding equation (4).

$$m_s \approx m_c\left(\left(\frac{r_s}{r_s - l_s}\right)^3 - 1\right) \quad (4)$$

Making the substitutions $m_c = m_O - m_{OSM}$, $m_s = m_O + (f_{WSM/OSM})m_{OSM} - m_C$, and $f_{WSM/OSM} = m_{WSM}/m_{OSM}$ (a ratio of hydrophilic monomer to hydrophobic monomer), where $m_O$ is a total mass of the oil components (e.g., the chlorpyrifos-methyl, the solvent and the hydrophobic monomer), $m_{OSM}$ is the mass of the hydrophobic monomer, and $m_{WSM}$ is the mass of the hydrophilic monomer, and solving for $m_{OSM}$ yields:

$$m_{OSM} = \frac{m_O\left(\left(\frac{r_s}{r_s - l_s}\right)^3 - 1\right)}{f_{WSM/OSM} + \left(\frac{r_s}{r_s - l_s}\right)^3} \quad (5)$$

For the determination of $m_{OSM}$, the entire quantity of $m_{WSM}$ was used in the calculation For example, the insecticidal formulations may be formed such that the shell of each microcapsule has an average thickness of between about 2 nanometers (nm) to about 50 nm and, more particularly, between about 2 nm to about 20 nm. For example, an average thickness of the shells may be about 10 nm.

One or more finishing agents may be added to the insecticidal capsule formulation. Such finishing agents include, for example, one or more surfactants, thickeners, preservatives, antifoaming agents and buffers. Examples of suitable surfactants include, but are not limited to, a graft copolymer of alkylphenolethoxylate and polyalkyleneglycoletheracryl, such as that commercially available from Croda Chemicals Ltd. (England) under the trade name ATLOX™ 4913 polymeric surfactant, GEROPON® sodium dioctyl sulfosuccinate (SDS), which is commercially available from Rhodia Novecare (Canbury, NJ) and GOHSENOL® GL03 polyvinyl alcohol. Suitable thickeners include, but are not limited to, xanthan gum (e.g., KELZAN® ASX xanthan gum, which may be obtained commercially from CP Kelco U.S., Inc., Atlanta, GA), a microcrystalline cellulose gel, such as AVICEL® CL 611, which is commercially available from FMC Corporation (Philadelphia, PA) and silicates (e.g., VEEGUM® magnesium aluminum silicate, which may be obtained commercially from R.T. Vanderbilt Company, Inc., Norwalk, CT). An example of a suitable preservative includes, but is not limited to, PROXEL® GXL preservative (Arch UK Biocides Limited, England). For example, GOHSENOL® GL03 polyvinyl alcohol, VEEGUM® magnesium aluminum silicate, KELZAN® ASX xanthan gum, and PROXEL® GXL preservative may optionally be added to the aqueous phase after foiination of the insecticidal capsule suspension.

An example of suitable antifoaming agents includes, but is not limited to, silicone-based anti-foaming agents. Such a silicon-based antifoaming agent is available from Harcros Chemicals, Inc. (Kansas City, KS) under the trade name Antifoam 100 IND. The buffer may include, for example, an aqueous solution of a weak acid and its conjugate base or a weak base and its conjugate acid. The buffer solution may be formulated to maintain a desired pH of the insecticide formulation.

The aqueous insecticidal capsule formulations may be optionally diluted in a carrier such as water and applied directly to, or to a surface adjacent to, a population of insects. The insecticidal formulations may be as effective against pests as the non-encapsulated formulations, but, in comparison, may exhibit significantly reduced toxicity to mammals, less environmental impact, and enhanced stability. Furthermore, the insecticidal formulations may maintain their insecticidal properties for a substantially increased time period in comparison to non-encapsulated formulations, especially liquid based formulations.

The following examples serve to explain embodiments of the present invention in more detail. These examples are not to be construed as being exhaustive or exclusive as to the scope of this invention.

EXAMPLES

Example 1

Preparation of Insecticidal Formulations

As illustrated in Table 1, formulations of insecticides, such as chlorpyrifos-methyl, may be incorporated into microcapsules by forming the capsule in the presence of an inert liquid, such as a hydrocarbon fluid and 1-nonanal. Various insecticidal formulations were prepared with different amounts of EDA in a continuous or in-line process as described herein.

TABLE 1

Example Insecticidal Capsule Formulations

|  | Formulation | | | |
|---|---|---|---|---|
|  | 1 | 2 | 8 | 11 |
| Chlorpyrifos-methyl | 19.4 | 19.4 | 19.4 | 19.4 |
| SOLVESSO ™ 150 ND hydrocarbon fluid | 19.0 | 19.0 | 19.0 | 19.0 |
| 1-nonanal | 0.38 | 0.38 | 0.38 | 0.38 |
| PAPI ® 27 polymethylene polyphenylisocyanate | 0.6231 | 0.6231 | 0.6231 | 0.6231 |
| Ethylenediamine (EDA) | 0.1604 | 0.1395 | 0.1256 | 0.0977 |
| GOHSENOL ® GL03 polyvinyl alcohol | 1.9886 | 1.9886 | 1.9886 | 1.9886 |
| GEROPON ® SDS | 0.2448 | 0.2448 | 0.2448 | 0.2448 |
| AVICEL ® CL 611 stabilizer | 0.11 | 0.11 | 0.11 | 0.11 |
| KELZAN ® ASX xanthan gum | 0.02 | 0.02 | 0.02 | 0.02 |
| PROXEL ® GXL preservative | 0.05 | 0.05 | 0.05 | 0.05 |
| Antifoam 100 IND | 0.0756 | 0.0756 | 0.0756 | 0.0756 |
| Deionized (DI) water | 34.7 | 34.7 | 34.7 | 34.7 |
| finishing water or optional buffer solution | 23.2475 | 23.2684 | 23.2823 | 23.3102 |
| Molar Ratio of Amine:Isocyante | 1.15 | 1.0 | 0.9 | 0.7 |
| totals: | 100 | 100 | 100 | 100 |

The aqueous phase was prepared by stirring together materials to make a 6.0 wt % polyvinyl alcohol solution (GOHSENOL® GL03), containing 0.15 wt % PROXEL® GXL with water as the balance ingredient. The organic or oil phase was prepared by stirring together 49.2% chlorpyrifos-methyl, 1.0% 1-nonanal, 48.2% SOLVESSO™ 150 and 1.6% PAPI™ 27. The cross-linking amine phase was prepared by dissolving EDA to make 2.0 wt % solution in water. The KELZAN® gel phase contained 1.5 wt % KELZAN® ASX, 0.1 wt % PROXEL® GXL and 98.4% water and was prepared using the recommended manufacturer's guideline for high shear dispersion. The AVICEL® gel phase contained 5.0 wt % AVICEL® CL-611, 0.1 wt % PROXEL® GXL and 94.9 wt % water dispersed together using high speed dispersion equipment. The buffer solution was prepared by mixing 50 mL of 0.1M potassium dihydrogen phosphate ($KH_2PO_4$) and 29.1 mL or 0.1M sodium hydroxide (NaOH) and bringing the solution to a final 100 mL volume with deionized water.

The in-line encapsulation system consisted of 3 metering pumps. Each pump was calibrated to deliver a fixed rate of material: 41.5 gram per minute (gpm) oil phase, 35.0 gpm aqueous phase and 2.9 gpm of the amine solution. The oil phase and aqueous phase pumps were combined at the inlet to an IKA DK-25 rotor/stator homogenizer which created the emulsion. The DK-25 had adjustable speed and a tachometer to permit fine particle size control. Typically, the DK-25 was operated at about 18,000 RPM. The EDA solution was metered into the liquid stream at the discharge of the homogenizer and passed through a 5 element static mixer and collected in a vessel. The rate of flow of the EDA solution was varied as needed to provide the desired ratio for each formulation. The formulation was finished by stirring for at least 30 minutes, then adding in the GEROPON® SDS, the Antifoam 100 IND, the KELZAN® and AVICEL® gel phases, the optional buffer solution, if used, and finally water as needed. A final brief homogenization was performed to incorporate the finishing agents into the capsule suspension.

By adjusting the mixing speed, it was possible to produce encapsulated organophosphate insecticidal formulations of varying capsule size having a broad range of shell thicknesses. Similarly, amounts of each of the isocyanate, the cross-linking amine, and the like, may be adjusted to create microencapsulated organophosphate insecticidal formulations having varying capsule sizes and shell thicknesses.

The molar ratios of amine:isocyanate groups in the emulsions containing EDA and polyisocyanate PAPI™ 27 used to prepare formulations 1, 2, 8 and 11 are respectively 1.15:1, 1.0:1, 0.9:1 and 0.7:1.

Example 2

Evaluation of the Insecticidal Formulations

Properties of the insecticide formulations formed from the ingredients listed in Table 1 (i.e., formulations 1, 2, 8 and 11) were determined over time. The properties evaluated were pH, particle size, viscosity and syneresis. Such properties were determined immediately after formation ("Initial"). Samples of each of the formulations 1, 2, 8 and 11 were stored at 54° C., 40° C., freezing temperature (FT, about 0° C.) and room temperature (RT, about 25° C.). The properties of the samples stored at 54° C., 40° C., FT and RT were determined after 2 weeks and the properties of the samples stored at 40° C. and RT were determined after 4 weeks. Tables 1 through 5 provide data showing a comparison of each of the properties of formulations 1, 2, 8 and 11 observed after storing each of the formulations as described.

The pH of the samples of formulations 1, 2, 8 and 11 stored at different temperatures for time periods of 2 weeks and 4 weeks were determined using conventional methods. A comparison of the pH of formulations 1, 2, 8 and 11 of the initial formulations and the samples stored at different temperatures for time periods of 2 weeks and 4 weeks are shown in Table 2. As shown in Table 2, the change in pH in each of formulations 1, 2, 8 and 11 was substantially consistent in the samples stored under substantially the same conditions. Thus, the molar ratio of amine:isocyanate groups used to prepare each of formulations 1, 2, 8 and 11 did not appear to greatly impact the pH level in the formulations as the differences were generally within a range of about 1 pH unit.

TABLE 2

Determination of pH of Insecticidal Capsule Formulations

| Time | Temperature | Formulation | | | |
|---|---|---|---|---|---|
| | | 1 | 2 | 8 | 11 |
| Initial | RT | 7.3 | 7.1 | 6.7 | 6.1 |
| 2 weeks | 54° C. | 4.2 | 3.9 | 4.1 | 4.2 |
| 2 weeks | 40° C. | 6.4 | 6.2 | 6.0 | 5.6 |
| 2 weeks | FT | 7.0 | 6.8 | 6.5 | 5.9 |
| 2 weeks | RT | 7.1 | 7.0 | 6.6 | 6.1 |
| 4 weeks | 40° C. | 5.6 | 5.5 | 5.4 | 5.2 |
| 4 weeks | RT | 7.0 | 6.8 | 6.5 | 5.9 |

Particle size distributions of the microcapsules in the samples of formulations 1, 2, 8 and 11 stored at different temperatures for time periods of 2 weeks and 4 weeks were determined using a MALVERN MASTERSIZER® 2000 light scattering particle sizer fitted with a small volume sample unit and using software version 5.12. Prior to measurement, the samples were shaken or stirred to ensure homogeneity. A comparison of the particle size measurements (μm, mean/90%) of the initial formulations and the samples stored at different temperatures for time periods of 2 weeks and 4 weeks are shown in Table 3. As shown in Table 3, the change in particle sizes in each of formulations 1, 2, 8 and 11 was substantially consistent in the samples stored under substantially the same conditions. Thus, the molar ratio of amine: isocyanate groups used to prepare each of formulations 1, 2, 8 and 11 does not appear to adversely impact the particle size.

TABLE 3

Determination of Particle Size of Insecticidal Capsule Formulations

| Time | Temperature | Formulation | | | |
|---|---|---|---|---|---|
| | | 1 | 2 | 8 | 11 |
| Initial | RT | 1.06 | 1.06 | 1.06 | 1.06 |
| 2 weeks | 54° C. | 3.5/6.3 | 3.7/6.7 | 3.8/6.9 | 3.4/6.1 |
| 2 weeks | 40° C. | 4.2/8 | 5.3/10.7 | 5.5/11.1 | 3.9/7.2 |
| 2 weeks | FT | 3.6/6.4 | 3.7/6.6 | 3.8/6.9 | 3.6/6.5 |
| 4 weeks | 40° C. | 3.5/6.3 | 3.6/6.5 | 3.8/6.9 | 3.5/6.1 |
| 4 weeks | RT | 3.8/6.6 | 4/7.2 | 3.9/7.1 | 3.7/6.6 |

Viscosities were determined for the samples of formulations 1, 2, 8 and 11 stored at different temperatures for time periods of 2 weeks and 4 weeks using an AR1000 viscometer from TA Instruments (New Castle, DE). A comparison of the viscosities in mPas (up/down at 100 s$^{-1}$) and syneresis (measured as the percent top clearing) of the initial formulations and the samples stored at different temperatures for time periods of 2 weeks and 4 weeks are shown in Tables 4 and 5.

TABLE 4

Determination of Viscosity of Insecticidal Capsule Formulations

| Time | Temperature | Formulation | | | |
|---|---|---|---|---|---|
| | | 1 | 2 | 8 | 11 |
| Initial | RT | 64/57 | 65/60 | 79/67 | 94/79 |
| 2 weeks | 54° C. | 72/65 | 73/65 | 77/64 | 74/58 |
| 2 weeks | 40° C. | 64/57 | 72/59 | 74/65 | 91/74 |
| 2 weeks | FT | 135/97 | 110/90 | 100/87 | 82/72 |
| 2 weeks | RT | 64/58 | 65/59 | 82/69 | 97/77 |
| 4 weeks | 40° C. | 70/64 | 71/59 | 72/62 | 83/69 |
| 4 weeks | RT | 64/56 | 63/57 | 78/66 | 93/78 |

As shown in Table 4, the viscosity of formulation 11 was maintained after storage at different temperatures for time periods of 2 weeks and 4 weeks in comparison to the viscosity of formulations 1, 2 and 8.

TABLE 5

Determination of Syneresis of Insecticidal Capsule Formulations

| Time | Temperature | Formulation | | | |
|---|---|---|---|---|---|
| | | 1 | 2 | 8 | 11 |
| 2 weeks | 54° C. | 28.6 | 17.0 | 18.9 | 12.0 |
| 2 weeks | 40° C. | 27.7 | 16.0 | 9.8 | 5.9 |
| 2 weeks | FT | 0.0 | 0.0 | — | 8.8 |
| 2 weeks | RT | 30.0 | 14.5 | 3.6 | 8.8 |
| 4 weeks | 40° C. | 28.3 | 22.0 | 17.0 | 10.6 |
| 4 weeks | RT | 29.4 | 21.6 | 7.4 | 3.9 |

As shown in Table 5, formulation 11 demonstrated substantially improved syneresis after storage at different temperatures for time periods of 2 weeks and 4 weeks in comparison to the amount of syneresis observed of formulations 1, 2 and 8.

Example 3

Chlorpyrifos-Methyl Degradation as a Function of Molar Ratio of Amine:Isocyanate Groups in the Cross-Linking Amine and Isocyanate Monomer Emulsion Used to Prepare Insecticidal Capsule Formulations Degradation of chlorpyrifos-methyl as a function of the molar ratio of amine:isocyanate groups in the cross-linking amine (EDA) and isocyanate monomer (PAPI™ 27) emulsion used to prepare the insecticidal capsule formulations was determined. In each of formulations 1, 2, 8 and 11, an amount of chlorpyrifos-methyl (in wt %) was determined in the samples stored at 54° C., 40° C., freezing temperature (FT, about 0° C.), and room temperature (RT, about 25° C.). The amount of the chlorpyrifos-methyl in each of the formulations was determined immediately after formation of the sample ("Initial"). Additionally, the amount of the chlorpyrifos-methyl in the samples stored at 54° C., 40° C., FT and RT was determined after 2 weeks and the amount of the chlorpyrifos-methyl in the samples stored at 40° C. and RT was determined after 4 weeks. Table 6 shows the amounts (in wt %) of the chlorpyrifos-methyl in each of the samples stored for the times and at the temperatures described.

Presented in FIG. 1 is a bar graph showing loss (in wt %) of chlorpyrifos-methyl in formulations 1, 2, 8 and 11 as a function of the molar ratio of amine:isocyanate groups in the cross-linking amine (EDA) and isocyanate monomer (PAPI™ 27) emulsion used to prepare the insecticidal capsule formulations following 2 weeks storage at 54° C. Formulation 1 (molar ratio of amine:isocyanate groups of about 1.15) exhibited a chlorpyrifos-methyl loss of about 4 wt %. Formulation 2 (molar ratio of amine:isocyanate groups of about 1) exhibited a chlorpyrifos-methyl loss of about 2.5 wt %. Formulation 8(molar ratio of amine:isocyanate groups of about 0.9) exhibited a chlorpyrifos-methyl loss of about 1.5 wt %. Formulation 11 (molar ratio of amine:isocyanate groups of about 0.7) exhibited a chlorpyrifos-methyl loss of about 0 wt %. Thus, reducing the molar ratio of the amine:isocyanate groups in the cross-linking amine (EDA) and isocyanate monomer (PAPI™ 27) emulsion used to prepare the insecticidal formulations results in a substantial reduction in the loss of chlorpyrifos-methyl.

TABLE 6

Determination of Chlorpyrifos-methyl (wt %) in Insecticidal Capsule Formulations After Storage at Various Temperatures

| | | Formulation | | | |
|---|---|---|---|---|---|
| Time | Temperature | 1 | 2 | 8 | 11 |
| Initial | RT | 20.2 | 20.3 | 20.3 | 20.1 |
| 2 weeks | 54° C. | 19.4 | 19.8 | 20.0 | 20.2 |
| 2 weeks | 40° C. | 20.1 | 20.2 | 20.1 | 20.2 |
| 2 weeks | FT | 19.2 | 20.1 | 20.0 | 19.9 |
| 2 weeks | RT | 20.2 | 20.2 | 20.3 | 20.1 |
| 4 weeks | 40° C. | 19.8 | 20.1 | 20.2 | 20.3 |
| 4 weeks | RT | 20.3 | 20.3 | 20.1 | 20.0 |

Example 4

Chlorpyrifos-Methyl Degradation as a Function of Capsule Wall Thickness while Maintaining the Molar Ratio of Amine:Isocyanate Groups in the Cross-linking Amine and Isocyanate Monomer Emulsion Used to Prepare Insecticidal Capsule Formulations at About 0.5:1

Formulations of chlorpyrifos-methyl (formulations A, B, C and D) were formed using substantially the same methods described in Example 1. Formulations A, B, C and D included RELDAN® insecticide as the source for the chlorpyrifos-methyl. The formulations were prepared using a molar ratio of amine:isocyanate in the emulsion used to prepare the microcapsules of about 0.5:1. The microcapsules of formulations A, B, C and D each had a particle size of about 3 µm and, respectively, had wall thicknesses of about 5 nm, about 10 nm, about 20 nm and about 100? nm.

The pH and loss of chlorpyrifos-methyl content of formulations A, B, C and D were determined over time. The properties were determined immediately after formation ("Initial"). Samples of each of the formulations A, B, C and D were stored at 54° C. and at room temperature (RT, about 25° C.). The properties of the samples were determined after 2 weeks in storage, after 4 weeks in storage and after 6 weeks in storage. Tables 7 and 8 provide data showing a comparison of each of the properties in formulations A, B, C and D observed after storing each of the formulations as described.

The pH of the samples of formulations A, B, C and D stored at different temperatures for time periods of 2 weeks, 4 weeks and 6 weeks was determined using conventional methods. A comparison of the pH of formulations A, B, C and D of the initial formulations and the samples stored at different temperatures for time periods of 2 weeks, 4 weeks and 6 weeks are shown in Table 7.

TABLE 7

Determination of pH of Insecticidal Capsule Formulations

| | pH | | | |
|---|---|---|---|---|
| Formulation (Wall thickness) | Initial | 6 weeks at RT | 2 weeks at 54° C. | 4 weeks at 54° C. |
| A (5 nm) | 6.0 | 5.2 | 2.5 | 2.30 |
| B (10 nm) | 6.9 | 6.0 | 2.5 | 2.12 |
| C (20 nm) | 7.4 | 6.8 | 2.9 | 2.08 |
| D (100 nm) | — | 6.4 | 6.0 | 5.9 |

As shown in Table 7, the pH of formulations A, B and C stored at 54° C. was substantially reduced after 4 weeks time and the pH of formulation D was substantially consistent in the samples stored under substantially the same conditions. Thus, reducing the particle size of the microcapsules in formulations A, B and C may adversely impact the pH level.

The loss of chlorpyrifos-methyl content in the samples of formulations A, B, C and D stored at different temperatures for time periods of 2 weeks, 4 weeks and 6 weeks were determined using conventional methods. A comparison of the loss of chlorpyrifos-methyl content in the samples of formulations A, B, C and D of the initial formulations and the samples stored at different temperatures for time periods of 2 weeks, 4 weeks and 6 weeks are shown in Table 7.

TABLE 8

Determination of the Loss of Chlorpyrifos-methyl Content of Insecticidal Capsule Formulations

| | Chlorpyrifos-methyl content (g/L) | | | | |
|---|---|---|---|---|---|
| | | 2 weeks at 54° C. | | 4 weeks at 54° C. | |
| Formulation (Wall thickness) | Initial | g/L | % loss | g/L | % loss |
| A (5 nm) | 201.8 | 196.5 | 2.6 | 189.0 | 6.3 |
| B (10 nm) | 203.0 | 194.5 | 4.2 | 187.0 | 7.9 |
| C (20 nm) | 202.1 | 188.3 | 6.8 | 179.8 | 11.0 |
| D (100 nm) | 196.2 | 196.2 | 0 | — | — |

As shown in Table 8, the loss of chlorpyrifos-methyl content in formulations A, B and C stored at 54° C. was substantially greater than for sample D after time in the samples stored under substantially the same conditions. Thus, reducing the microcapsule wall thickness in each of formulations A, B and C may increase the loss of chlorpyrifos-methyl content in those samples.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:
1. An insecticide formulation, comprising:
a polymer shell formed from a mixture comprising a cross-linking ethylenediamine and an isocyanate where the molar ratio of ethylenediamine:isocyanate groups is between 0.3 to 1 and 0.8 to 1;
an insecticide at least partially encapsulated by the polymer shell; and
a continuous aqueous phase.

2. The insecticide formulation of claim 1, wherein the insecticide comprises an organophosphate selected from the group consisting of: acephate, azinphos-methyl, chlorfenvinphos, chlorethoxyfos, chlorpyrifos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and trichlorfon.

3. The insecticide formulation of claim 1, wherein the insecticide comprises chlorpyrifos-methyl.

4. The insecticide formulation of claim 1, wherein the molar ratio of ethylenediamine to isocyanate groups is 0.7 to 1.

5. The insecticide formulation of to claim 1, wherein the polymer shell has a thickness between 2 nm and 20 nm.

6. A method of forming an insecticide formulation, comprising:
   combining an aqueous phase and an oil phase comprising an isocyanate monomer and at least one insecticide;
   emulsifying the oil phase and the aqueous phase to form a mixture;
   adding a cross-linking ethylenediamine to the mixture, the mixture comprising a molar ratio of ethylenediamine to isocyanate groups of between 0.3 to 1 and 0.8 to 1; and
   reacting the isocyanate monomer with the cross-linking ethylenediamine to form the insecticide formulation.

7. The method of claim 6, further comprising dissolving one or more of a surfactant and a preservative in water to form the aqueous phase.

8. The method of claim 7, wherein dissolving one or more of a surfactant and a preservative in water to form the aqueous phase comprises dissolving polyvinyl alcohol and a preservative in the water.

9. The method of claim 6, further comprising combining an isocyanate monomer, 1-nonanal and a solution comprising chlorpyrifos-methyl in a solvent to form the organic phase.

10. The method of claim 9, wherein the isocyanate monomer is a polymethylene polyphenylisocyanate.

11. The method of claim 6, wherein emulsifying the oil phase and the aqueous phase to form a mixture comprises emulsifying the oil phase and the aqueous phase to form a plurality of particles of the oil phase within the aqueous phase.

12. The method of claim 6, wherein adding a cross-linking ethylenediamine to the mixture comprises forming the reaction mixture to comprise a molar ratio of ethylenediamine to isocyanate groups of 0.7 to 1.

13. The method of claim 6, wherein reacting the isocyanate monomer with the cross-linking ethylenediamine to form the insecticide formulation comprises exposing the monomer and the cross-linking ethylenediamine to a temperature of between about 20° C. and about 60° C.

14. A method of forming an insecticide formulation, comprising:
   forming an oil phase consisting of an aromatic isocyanate monomer, at least one insecticide composition, at least one solvent, and at least one preservative;
   combining the oil phase with an aqueous phase to form a mixture; and
   combining ethylenediamine with the mixture to form the insecticide formulation, wherein a molar ratio of the ethylenediamine:aromatic isocyanate monomer is between 0.3 to 1 and 0.8 to 1.

15. The method of claim 14, wherein forming an oil phase consisting of an aromatic isocyanate monomer, at least one insecticide composition, at least one solvent, and at least one preservative comprises forming an organic phase consisting of an isocyanate monomer, chlorpyrifos-methyl, a solvent, and 1-nonanal.

16. The method of claim 14, further comprising selecting a polymethylene polyphenylisocyanate as the isocyanate.

17. The method of claim 14, wherein combining the organic phase with an aqueous phase to form a mixture comprises emulsifying the oil phase and the aqueous phase to form a plurality of particles of the oil phase within the aqueous phase.

18. The method of claim 17, wherein emulsifying the oil phase and the aqueous phase to form a plurality of particles of the oil phase within the aqueous phase comprises emulsifying the oil phase and the aqueous phase to form a plurality of particles having an average diameter of between 1 μm and 30 μm.

19. The method of claim 14, further comprising selecting an organophosphate insecticide composition as the at least one insecticide composition.

20. A method of extending the effective field life of an insecticide, comprising:
   combining the insecticide, a cross-linking ethylenediamine, and at least one isocyanate monomer where the ethylenediamine and the isocyanate groups are present at a molar ratio between 0.3:1 and 0.8:1; and
   forming a polymer shell that at least partially encapsulates a portion of the insecticide.

21. The method of claim 20, wherein combining the insecticide, a cross-linking ethylenediamine, and at least one isocyanate monomer comprises combining an organophosphate, the cross-linking ethylenediamine, and the at least one isocyanate monomer.

22. The method of claim 20, wherein the insecticide is chlorpyrifos-methyl.

23. The method of claim 20, wherein forming a polymer shell that at least partially encapsulates a portion of the insecticide comprises:
   forming an oil phase comprising the insecticide and the at least one isocyanate monomer;
   combining the oil phase with an aqueous phase to form a mixture; and
   combining the cross-linking ethylenediamine with the mixture to form the microencapsulated insecticidal formulation.

24. The method of claim 23, wherein forming an oil phase comprising the insecticide and the at least one isocyanate monomer comprises forming an oil phase consisting of the insecticide, the at least one isocyanate monomer and a solvent.

25. The method of claim 23, wherein combining the oil phase with an aqueous phase to form a mixture comprises combining the oil phase with an aqueous phase comprising water and a surfactant to form the mixture.

26. A method for controlling an insect population, comprising:
   forming an insecticide formulation, comprising:
      combining an aqueous phase and an oil phase comprising a hydrophobic isocyanate monomer and at least one insecticide to form a mixture;
      adding a cross-linking ethylenediamine to the mixture, forming a reaction mixture comprising a molar ratio of ethylenediamine to isocyanate groups of between 0.3:1 and 0.8:1; and
      reacting the hydrophobic isocyanate monomer with the cross-linking ethylenediamine to form the insecticide formulation; and applying the insecticide formulation to an area containing or adjacent to a population of insects.

27. A stable aqueous insecticide formulation comprising:
a) a microcapsule, having a water insoluble polyurea shell wall prepared by an interfacial polycondensation reaction between a water soluble cross-linking ethylenediamine and an oil soluble isocyanate monomer in which
   (i) the molar ratio of ethylenediamine to isocyanate groups is between 0.3 to 1 and 0.8 to 1,
   (ii) the polyurea shell has a thickness of greater than about 2 nanometers (nm) and less than about 50 nm,
   (iii) the average particle size is from 1 micrometer (µm) to 30 µm, and
   (iv) containing an inner liquid core comprised of an insecticide at least partially encapsulated by the polymer shell; and
b) a continuous aqueous phase.

* * * * *